(12) United States Patent
Couvreur et al.

(10) Patent No.: US 9,295,630 B2
(45) Date of Patent: Mar. 29, 2016

(54) VITAMIN C COMPLEXES

(71) Applicants: CENTRE NATIONAL DE LA RECHERCHE SCIENTIFIQUE, Paris (FR); UNIVERSITË PARIS SUD (PARIS XI), Orsay (FR)

(72) Inventors: Patrick Couvreur, Villebon Sur Yvette (FR); Fatima Zouhiri, Chatenay-Malabry (FR); Ruxandra Gref, Verrieres Le Buisson (FR); Didier Desmaele, Fresnes (FR)

(73) Assignees: CENTRE NATIONAL DE LA RECHERCHE SCIENTIFIQUE, Paris (FR); UNIVERSITE PARIS SUD XI, Orsay (FR)

( * ) Notice: Subject to any disclaimer, the term of this patent is extended or adjusted under 35 U.S.C. 154(b) by 0 days.

(21) Appl. No.: 14/385,708

(22) PCT Filed: Mar. 14, 2013

(86) PCT No.: PCT/IB2013/052031
§ 371 (c)(1),
(2) Date: Sep. 16, 2014

(87) PCT Pub. No.: WO2013/136294
PCT Pub. Date: Sep. 19, 2013

(65) Prior Publication Data
US 2015/0045426 A1  Feb. 12, 2015

(30) Foreign Application Priority Data
Mar. 16, 2012  (FR) ..................... 12 52382

(51) Int. Cl.
| A61K 31/34 | (2006.01) |
| B32B 5/16 | (2006.01) |
| C07D 307/62 | (2006.01) |
| A61K 8/67 | (2006.01) |
| A61Q 19/08 | (2006.01) |
| A61K 8/02 | (2006.01) |

(52) U.S. Cl.
CPC ............ *A61K 8/676* (2013.01); *A61K 8/0241* (2013.01); *A61Q 19/08* (2013.01); *C07D 307/62* (2013.01); *A61K 2800/413* (2013.01); *A61K 2800/652* (2013.01); *Y10T 428/2982* (2015.01)

(58) Field of Classification Search
CPC ........... A61Q 19/08; A61K 2800/652; A61K 8/0241; A61K 2800/413; A61K 8/676; C07D 307/62
USPC .............. 514/474; 428/402; 549/315
See application file for complete search history.

(56) References Cited

U.S. PATENT DOCUMENTS

| 4,997,958 A | 3/1991 | Pauling et al. |
| 5,489,589 A | 2/1996 | Wittman et al. |
| 2004/0092428 A1 | 5/2004 | Chen et al. |
| 2006/0198940 A1 | 9/2006 | McMorrow |

FOREIGN PATENT DOCUMENTS

| EP | 0 296 483 A2 | 6/1988 |
| JP | A-2012-001457 | 1/2012 |
| WO | WO 2006/019186 A1 | 2/2006 |
| WO | WO 2006/090029 A1 | 8/2006 |
| WO | WO 2009/071850 A2 | 6/2009 |
| WO | WO 2009/150344 A1 | 12/2009 |
| WO | WO 2010/049899 A1 | 5/2010 |
| WO | WO 2010/049900 A1 | 5/2010 |

OTHER PUBLICATIONS

Ceruti et al., "Synthesis of (E)- and (Z)-29-methylidyne-2,3-oxidosqualene derivatives as inhibitors of liver and yeast oxidosqualene cylase," J. Chem. Soc., Perkin Trans 1, 2002, 1477-1486.
Fessi et al., "Nanocapsule formation by interfacial polymer deposition following solvent displacement," International Journal of Pharmaceutics, 55 (1989) R1-R4.
Van Tamelen, "Bioorganic Chemistry: Sterols and Acyclic Terpene Terminal Epoxides," Bioorganic Chemistry, 1968, pp. 111-120.
Couvreur et al., "Squalenoyl Nanomedicines as Potential Therapeutics," Nano Letters, 2006, vol. 6, No. 11, pp. 2544-2548.

(Continued)

*Primary Examiner* — T. Victor Oh
(74) *Attorney, Agent, or Firm* — Oliff PLC

(57) ABSTRACT

A complex formed of at least one molecule of 5-(1,2-dihydroxy-ethyl)-3,4-dihydroxy-5H-furan-2-one or a derivative covalently bonded with at least one hydrocarbon radical with formula (A) as follows: wherein: •-m 1=1, 2, 3, 4, 5 or 6; •-m 2=0, 1, 2, 3, 4, 5 or 6; and represents the site of the bond with the molecule of 5-(1,2-dihydroxy-ethyl)-3,4-dihydroxy-5H-furan-2-one or derivative. Formula (I)

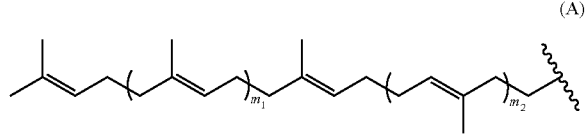

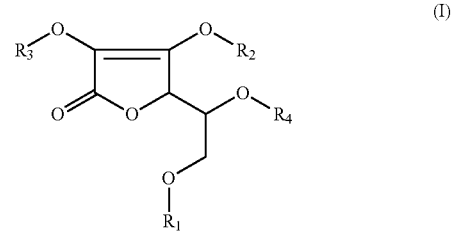

22 Claims, No Drawings

(56) References Cited

OTHER PUBLICATIONS

Bhatt et al., "Accumulation of E,E,E-Triene by the Monensin-Producing Polyketide Synthase when Oxidative Cyclization is Blocked," Angewandte Chemie, 2005, vol. 117(43), pp. 7237-7240.

Pala et al., "Terpene Compounds as Drugs," Arzneim.-Forsch., 1970, pp. 62-28

Relas et al., "Fate of intravenously administered squalene and plant sterols in human subjects," J. Lipid Research, 2001, vol. 42, pp. 988-994.

Strandberg et al., "Metabolic variables of cholesterol during squalene feeding in humans: comparison with cholestyramine treatment," J. Lipid Research, 1990, vol. 31, pp. 1637-1643.

Trommer et al., "Overcoming the Stratum Corneum: The Modulation of Skin Penetration," Skin Pharmacology and Physiology, vol. 19, 2006, pp. 106-121.

Bekkara-Aounallah et al., "Novel PEGylated nanoassemblies made of self-assembled squalenoyl nucleoside analogues," Advanced Functional Materials, vol. 18, 2008, pp. 3715-3725.

Jun. 5, 2013 International Search Report issued in PCT Application No. PCT/IB2013/052031 (with English translation).

Jun. 5, 2013 Written Opinion of the International Searching Authority issued in PCT Application No. PCT/IB2013/052031 (with English Translation).

May 15, 2012 French Preliminary Search Report issued in FR 1252382.

May 15, 2012 French Written Opinion issued in FR 1252382.

VITAMIN C COMPLEXES

The present invention proposes a novel bioconjugate of vitamin C that is particularly interesting for its activity on the skin. The present invention also relates to methods for preparation thereof, compositions comprising it as well as use thereof in the cosmetic, dermatological, pharmaceutical and food areas.

Human skin consists of two compartments, namely a surface compartment, the epidermis, and a deep compartment, the dermis, which provides a solid support for the epidermis.

The dermis, a tissue that supplies nutrients to the epidermis, mainly consists of fibroblasts and an extracellular matrix, itself mainly composed of collagen, elastin and a substance, called ground substance, components synthesized by the fibroblast.

The fibroblasts synthesize predominantly collagens, matrix glycoproteins other than collagens (fibronectin, laminin), proteoglycans and elastin. The keratinocytes synthesize predominantly sulfated GAGs and hyaluronic acid.

Regarding the extracellular matrix of the dermis, it is, like all the body's connective tissues, composed of proteins belonging to several broad families: collagens, matrix glycoproteins other than collagens (fibronectin, laminin), elastin and proteoglycans (PGs). There are also glycosaminoglycans (GAGs) in free form (i.e. not bound to a protein).

The components of the extracellular matrix notably play an important role in the mechanical properties of the skin, in particular its tonicity, firmness, elasticity and flexibility.

Collagen is a protein made up of three alpha polypeptide chains joined by hydrogen bonds between hydroxylysine and hydroxyproline and associated covalent bonds. According to the various possible combinations, there are several types of collagen with their own particular structures, which are found in particular organs.

Among these types of collagen, we may notably mention type I collagen and type III collagen, which are located predominantly in the dermis. Type I collagen notably contributes to the rigidity and strength of the tissues. With increasing age, it becomes more and more predominant (more than 80%). Thus, the fibers become more rigid and less flexible, leading to a loss of firmness of the skin.

Regarding type III collagen, also called "collagen of youth", it is synthesized in abundance during fetal life and in adolescence.

However, it was found that with increasing age, the amount of type III collagen decreases to the benefit of type I collagen (Wang et al., African J. Biotechn., 2011, Vol. 10(13),2524-2529).

Moreover, it is known that vitamin C, also known as ascorbic acid, 5-(1,2-dihydroxy-ethyl)-3,4-dihydroxy-5H-furan-2-one or 3-keto-L-gulofuranolactone, is involved in hundreds of processes in the body.

It is also known that vitamin C notably has the function of helping the body to manufacture collagen, essential to formation of the connective tissue of the skin, ligaments and bones.

Generally an organism is supplemented with vitamin C by the oral route, classically via food and more occasionally via food supplements enriched with vitamin C. More recently, it has been proposed to administer vitamin C topically, notably for purposes of improving the aesthetic appearance of the skin.

Unfortunately, vitamin C is also known to be one of the most fragile vitamins. Thus, it is sensitive to heat, is averse to basic environments and especially is very sensitive to the oxygen of the air.

Consequently, most of the existing formulations comprising vitamin C must generally contain stabilizers or preservatives in order to prevent any degradation of the latter prior to use.

Moreover, vitamin C as such has a low capacity for penetrating into the skin notably on account of its hydrophilic character.

To make up for this lack of permeability of ascorbic acid in the epidermis and dermis of the skin, international application WO 2006/019186 proposes employing, in care products applied topically and food products for application by the oral route, fat-soluble derivatives comprising vitamin C in a form coupled in its position 6 to a polyunsaturated fatty acid (6-O-PUFA). Other derivatives of vitamin C such as the esters of $C_2$-$C_{20}$ aliphatic carboxylic acids in position 6 of ascorbic acid such as 6-ascorbyl palmitate and 6-ascorbyl linoleate are also described in patent U.S. Pat. No. 4,997,958 but for antioxidant purposes.

However, as follows from the tests presented below, derivatives as described in documents WO 2006/019186 and U.S. Pat. No. 4,997,958 are not found to be totally satisfactory in terms of penetration into the deep layers of the skin.

Moreover, these derivatives that are already known are not entirely satisfactory with regard to cytotoxicity and some of them are not always suitable for a formulation at high concentration. For example, the compound 6-ascorbyl palmitate formulated in an oil is no longer—beyond 5 wt %, expressed as weight of vitamin C active ingredient relative to the total weight of the composition—in the form of a homogeneous formulation and has a tendency to crystallize. These drawbacks make this compound particularly ineffective in an oily formulation, which is, for obvious reasons, a galenical formula that is particularly desirable for topical administration.

The aim of the present invention is precisely to propose novel derivatives of vitamin C that are satisfactory in these respects.

Thus, according to one of its aspects, the present invention aims to supply novel derivatives of vitamin C that penetrate into the skin more easily and make it possible to improve the beneficial effect of vitamin C in the deep layers of the skin.

According to another of its aspects, the present invention aims to propose novel derivatives of vitamin C able to display increased stability against oxidation.

According to yet another of its aspects, the present invention aims to propose novel derivatives of vitamin C able to stimulate expression of collagen, and more particularly of type III collagen.

According to yet another of its aspects, the present invention aims to supply novel derivatives of vitamin C able to stimulate expression of GAGs.

According to yet another of its aspects, the present invention aims to propose novel derivatives of vitamin C, favorable for formulation both in an aqueous medium and in an oily medium, capable of being formulated homogeneously, even for large amounts of vitamin C equivalent.

According to yet another of its aspects, the present invention aims to propose novel derivatives of vitamin C compatible with any method of administration and satisfactory in terms of safety.

Finally, according to another of its aspects, the present invention aims to supply novel derivatives of vitamin C capable of improving the general morphology of the skin in terms of flexibility, hydration, thickness, and elasticity.

Against all expectations, the present inventors found that the covalent coupling of ascorbic acid with at least one specific molecule precisely offers satisfaction in these respects.

Thus, the present invention relates to a complex formed from at least one molecule of 5-(1,2-dihydroxy-ethyl)-3,4-dihydroxy-5H-furan-2-one or derivative bound covalently to at least one hydrocarbon radical of formula (A) as follows:

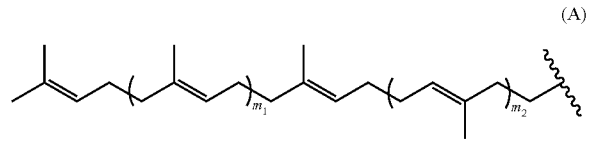

(A)

in which:
$m_1$=1, 2, 3, 4, 5 or 6;
$m_2$=0, 1, 2, 3, 4, 5 or 6; and

represents the bond to the molecule of 5-(1,2-dihydroxy-ethyl)-3,4-dihydroxy-5H-furan-2-one or derivative.

In the sense of the invention, the term complex or conjugate will be used synonymously to denote the product of coupling between at least one molecule of 5-(1,2-dihydroxy-ethyl)-3,4-dihydroxy-5H-furan-2-one or derivative and at least one hydrocarbon radical of formula (A).

In the sense of the invention, the term "bond" associated with the symbol

signifies that

symbolizes the site of binding of the entity of formula (A) to the entity ascorbic acid or derivative. Thus, as described in detail below, the binding site may be involved either directly in a single covalent bond between entity (A) and the entity ascorbic acid or derivative, or can be represented by a function resulting from the interaction between two reactive functions, for example between a carboxyl function and an alcohol function, or else can be represented by a group of the spacer type.

Thus, entity (A) and the entity ascorbic acid or derivative may be bound either to each other via a covalent bond or via a spacer group or a function of the ester, ether, phosphate or amide type, as described below.

According to another aim, the invention relates to a complex or conjugate as defined above, in which the hydrocarbon compound or radical comprises from 12 to 40 carbon atoms, preferably from 18 to 30 carbon atoms.

As presented in more detail below, said hydrocarbon compound or radical may advantageously be derived from squalene, farnesol or geraniol and more preferably from squalene.

Advantageously, the two types of entities forming the complex defined above are coupled by a covalent bond of the ester, ether, phosphate or amide type, and preferably ester.

The present invention also relates to an oily formulation comprising a complex or conjugate as described above. More particularly, this formulation is in the form of a gel that may contain up to at least 3 wt %, or even at least 10 wt %, expressed as weight of vitamin C active ingredient, relative to the total weight of the composition.

According to a preferred variant, the oil considered for formulating the complex according to the invention in the form of said gel is squalene or a derivative thereof.

According to another of its aspects, the present invention relates to nanoparticles of a complex or conjugate as described above.

In fact, against all expectations, the inventors found that the conjugate according to the invention is capable of self-assembly, i.e. of self-organizing spontaneously in an aqueous medium in the form of nanoparticles that possess at least the same activities as the conjugate as such.

Thus, the present invention also relates to a method of preparing said nanoparticles comprising at least dispersing a complex according to the present invention, in at least one organic solvent, at a concentration sufficient to obtain, on adding the corresponding mixture to an aqueous phase, with stirring, the instantaneous formation of nanoparticles in suspension in said aqueous phase, and, if required, isolation of said nanoparticles.

The capacity of the complexes according to the invention for self-organizing in the form of nanoparticles according to the present invention constitutes an alternative that is advantageous in several respects.

Firstly, the nanoparticulate state of the vitamin C complex according to the invention advantageously allows the latter to be formulated to be homogeneous in a stabilized manner in an aqueous medium.

Furthermore, as follows from the tests presented below, the nanoparticulate state of the vitamin C complex according to the invention makes it possible to increase the penetration of the latter as far as the deep layers of the skin. This improvement in penetration into the deep layers of the skin advantageously makes it possible to use lower concentrations of vitamin C than those usually required.

Moreover, the nanoparticles according to the invention advantageously make it possible to stimulate expression of collagen and more precisely of type III collagen, as well as GAGs, as pointed out above, and improve the general morphology of the skin.

Moreover, taking into account the small size of the particles of conjugates considered according to the invention, this particular form can be administered in the form of an aqueous suspension by the parenteral (or injectable) route and notably intravenously.

Thus, advantageously, the average size of these nanoparticles is in the range from 30 nm to 500 nm, in particular from 40 to 250 nm, or even from 45 to 95 nm.

Nanoparticles of conjugates formed by coupling of at least one hydrocarbon radical, and in particular squalene, with an active ingredient such as gemcitabine, nucleosides, nucleic acids, statins, taxoids, doxorubicin, epirubicin and beta-lactam have already been described in documents WO 2006/090029, Couvreur et al., Nano Lett. 2006, 6, pp. 2544-25 48, WO 2009/150344, WO 2009/071850, WO 2010/049899 and WO2010/049900.

However, these active ingredients are clearly very different structurally from vitamin C.

The present invention also relates to a cosmetic, dermatological or food composition comprising as active substance at least one complex according to the invention and/or nanoparticles according to the invention, together with at least one physiologically acceptable vehicle.

According to another aim, the invention relates to the cosmetic use of a complex according to the invention and/or of nanoparticles according to the invention for preventing and/or treating the signs of aging of the skin of the body and/or of the face.

For example, a cosmetic composition according to the invention may be used for preventing and/or treating wrinkles and/or lines, withered skin, lack of elasticity and/or of tonus of the skin, thinning of the dermis, degradation of collagen fibers, slack skin, thin skin and/or internal degradation of the skin resulting from exposure to ultraviolet radiation.

According to another aim, the present invention aims to protect the cosmetic use of a complex or conjugate according to the invention and/or of nanoparticles according to the invention for stimulating the synthesis of collagen, in particular type III collagen, and/or for stimulating the synthesis of glycosaminoglycans.

The present invention also relates to a complex or conjugate according to the invention and/or nanoparticles according to the invention for use in medicine and more precisely in the prevention and/or treatment of burns and/or wounds and/or any other disorder connected with healing of the dermis and/or epidermis.

According to yet another aim, the present invention relates to a method of cosmetic treatment of the skin of the body and/or of the face and/or of the scalp, in which a composition as defined above is administered.

Complex According to the Invention

As stated above, the complexes according to the invention are formed by coupling a vitamin C molecule or analog to at least one specific hydrocarbon radical.

Hydrocarbon Radical

In the sense of the present invention, the hydrocarbon radical corresponds to formula (A) as follows:

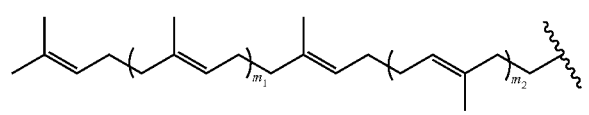

(A)

in which:
m$_1$=1, 2, 3, 4, 5 or 6;
m$_2$=0, 1, 2, 3, 4, 5 or 6; and

represents the site of binding to the molecule the molecule of 5-(1,2-dihydroxy-ethyl)-3,4-dihydroxy-5H-furan-2-one or derivative.

This hydrocarbon radical is generally derived from putting in the presence of at least one molecule of compound of formula (A'):

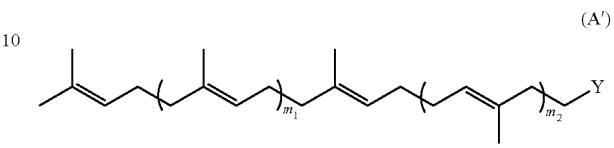

(A')

in which:
Y represents a reactive function and notably of the alcohol, carboxylic acid, or phosphate type; and
m$_1$ and m$_2$ are as defined for the radical of formula (A).

The hydrocarbon compound of formula (A') comprises at least 12 carbon atoms, in particular from 12 to 40 carbon atoms and preferably from 18 to 30 carbon atoms.

Advantageously, the compounds of formula (A') are selected from the compounds of formula (A') in which:
m$_1$ represents 1, m$_2$ represents 2 and Y is a —COOH function,
m$_1$ and m$_2$ represent 0 and Y is a —COOH function, and
m$_1$ represents 1, m$_2$ represents 0 and Y is a —COOH function.

More precisely, a compound of formula (A) that can be used for forming a conjugate according to the present invention is squalene (also called spinacene or supraene), which is an essential intermediate in the biosynthesis of cholesterol.

Chemically, it is also called (E)2,6,10,15,19,23-hexamethyl-2,6,10,14,18,22-tetracosahexene of the following formula:

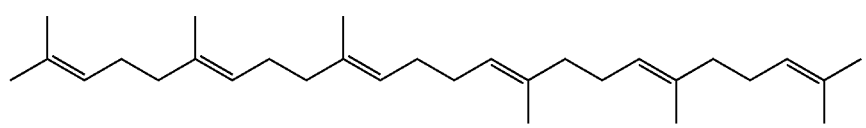 [SMILES: CC(C)=CCC/C(C)=C/CC/C(C)=C/CC/C=C(\C)CC/C=C(\C)CCC=C(C)C]

In this preferred embodiment of the invention, the hydrocarbon radical present in a conjugate according to the present invention is a radical of formula (A) in which m$_1$=1 and m$_2$=2.

Another compound useful for forming a complex according to the present invention is farnesol, which is an acyclic sesquiterpene alcohol.

Chemically, it is also called (2E, 6E)-3,7,11-trimethyl-dodeca-2,6,10-trien-1-ol of the following formula:

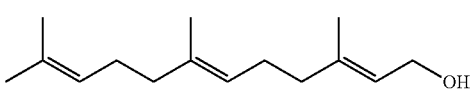 [SMILES: CC(C)=CCC/C(C)=C/CC/C(C)=C/CO]

In this other embodiment of the invention, the hydrocarbon radical present in a complex according to the present invention is a radical of formula (A) in which m$_1$=1 and m$_2$=0.

Yet another compound that can be used for forming a conjugate according to the present invention is geraniol (also called rhodinol) which is an unsaturated terpene alcohol.

Chemically, it is also called (2E)-3,7-dimethylocta-2,6-dien-1-ol of the following formula:

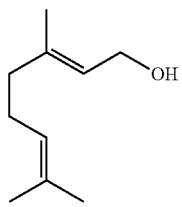

In this other embodiment of the invention, the hydrocarbon radical present in a complex according to the present invention is a radical of formula (A) in which $m_1=0$ and $m_2=0$.

According to a preferred embodiment of the present invention, the hydrocarbon derivative present in a complex according to the present invention is a squalene derivative.

To illustrate hydrocarbon compounds able to form a complex containing at least one squalene derivative according to the present invention, we may more particularly mention squalenic acid and derivatives thereof such as 1,1',2-tris-norsqualenic acid, 1,1',2-tris-norsqualenamine, 1,1',2-tris-norsqualenol, 1,1',2-tris-norsqualethiol, squalenacetic acid, squalenylethanol, squalenylethanethiol, squalenylethylamine.

In particular, a conjugate according to the present invention will be able to contain at least one radical derived from the covalent coupling of a molecule of 1,1',2-tris-norsqualenic acid.

In particular, a conjugate according to the present invention will be able to contain at least one radical derived from the covalent coupling of a molecule of 1,1',2-tris-norsqualenol.

Alternatively, a conjugate according to the present invention may comprise at least two hydrocarbon radicals according to the present invention.

Vitamin C

Structurally, vitamin C and derivatives thereof in the sense of the invention have in common a 3,4-dihydroxy-5H-furan-2-one system that can be represented schematically by the following unit.

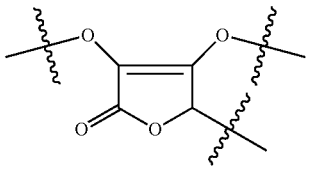 [SMILES: *OC1=C(O*)C(*)OC1=O]

Consequently, the complexes according to the invention advantageously possess said unit.

More precisely, vitamin C is represented by formula (IV) and its tautomeric form as follows.

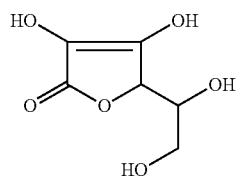

Compounds of general formula (IV) may comprise one or more asymmetric carbons. They may therefore exist in the form of enantiomers or diastereoisomers. These enantiomers, diastereoisomers, and mixtures thereof, including the racemic mixtures, form part of the invention.

The compounds with the aforementioned formulas may exist in the form of acids or of salts of addition to bases.

These salts are advantageously prepared with pharmaceutically acceptable bases, but the salts of other bases, useful for example for purification or separation of the compounds with the aforementioned formulas, also form part of the invention.

The compounds of general formula (IV) may, moreover, be in the form of hydrates or solvates, namely in the form of associations or combinations with one or more molecules of water or with a solvent. Such hydrates and solvates also form part of the invention.

Advantageously, according to the present invention, ascorbic acid, sodium ascorbate, potassium ascorbate and/or calcium ascorbate, and preferably ascorbic acid, may be complexed.

Vitamin C/Hydrocarbon Radical Complex

According to a particular embodiment, the conjugate according to the invention is of general formula (I)

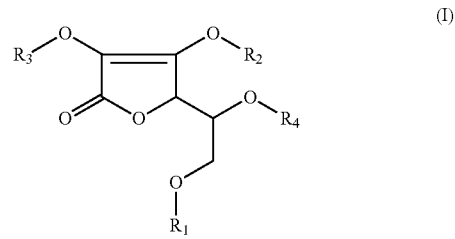

in which:

$R_1$, $R_2$, $R_3$ and $R_4$, which may be identical or different, represent independently of one another a hydrogen atom or a hydrocarbon radical of formula (A) as defined above, with at least one of the groups $R_1$, $R_2$, $R_3$ and $R_4$ being different from the hydrogen atom.

The derivatives of formula (I) according to the invention in which $R_2$ is a hydrogen atom are illustrated by the following general formula (I'):

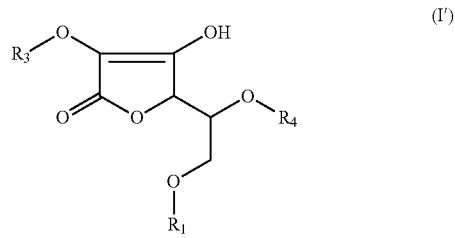

in which $R_1$, $R_3$ and $R_4$ are as defined above, at least one of the groups $R_1$, $R_3$ and $R_4$ being different from the hydrogen atom.

According to another particular embodiment, the conjugate according to the invention is of general formula (IA)

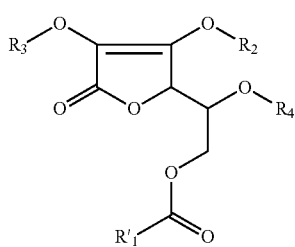

(IA)

in which:
R$_2$, R$_3$ and R$_4$ are as defined above and R'$_1$ represents a hydrocarbon radical of formula (A) as defined above.

Advantageously, the complex or conjugate according to the invention is of general formula (IA) in which all three of R$_2$, R$_3$ and R$_4$ represent a hydrogen atom.

The hydrocarbon radicals according to the invention are generally fixed by a covalent bond at the level of the hydroxyl group carried by carbon atom 2 and/or 3 and/or 4 and/or 5 and/or 6 of ascorbic acid, and preferably at the level of the hydroxyl group carried by carbon atom 6 of ascorbic acid, or at the level of the hydroxyl group carried by carbon atom 2 of ascorbic acid, or at the level of the hydroxyl group carried by carbon atom 3 of ascorbic acid.

Of course, the complexes of ascorbic acid according to the present invention may be complexes comprising two derivatizations, three derivatizations, or even four derivatizations, and the latter may be identical or different.

As stated above, formation of the vitamin C/hydrocarbon radical complex according to the invention requires that the two entities brought into contact respectively bear a so-called reactive function, i.e. able to form the expected covalent bond by their interaction. These functions may or may not be naturally present on the two starting entities. If they are not, the starting entity will have to undergo a modification, prior to the coupling reaction.

More precisely, the hydrocarbon compound according to the invention generally bears a function capable of reacting with a function present on the vitamin C molecule in question, so as to establish a covalent bond between the two entities, for example of the ester, ether, phosphate or amide type, thus forming a covalent complex.

Advantageously, it is an ester function. For example, the hydrocarbon compound able to react with a vitamin C molecule or a derivative thereof to form the aforementioned complex is 1,1',2-tris-norsqualenic acid or a derivative thereof, for example its acid halide and more particularly the acid chloride, or its anhydride mixed with ethyl chloroformate. Preferably, the acid chloride derived from 1,1',2-tris-norsqualenic acid is used.

According to another variant, it is an ether function. For example, the hydrocarbon compound able to react with a vitamin C molecule or a derivative thereof to form the aforementioned conjugate is 1,1',2-tris-norsqualenol or a derivative thereof, for example 1,1',2-tris-norsqualenol mesylate.

According to another embodiment, the covalent bond that exists between the two types of molecules may be represented by a functional spacer or linkage. Such a linkage may notably prove useful for increasing the strength of the vitamin C/hydrocarbon radical interaction.

Such a linkage may also be advantageous for introducing, via each of the two ends of its backbone, the appropriate functions, i.e. respectively possessing the expected reaction affinity, one for the function present on the compound with hydrocarbon structure according to the invention, and the other for the function present on the vitamin C molecule in question.

It may also be envisaged that this linkage additionally possesses, at the level of its backbone, a labile function, favorable subsequently for separation of the compound with hydrocarbon structure from the vitamin C molecule in question. It may for example be a peptide unit recognizable by an enzyme.

Units of the linkage type are well known by a person skilled in the art and their application is clearly within his capabilities.

As representative examples of linkages that may be envisaged according to the invention, we may notably mention alkylene chains, (poly)amino acid units, polyols, saccharide units, and polyethylene glycol (polyether oxides).

The following definitions are used in the sense of the present invention:
"alkylene chain", a C$_1$-C$_4$ alkylene group, i.e. a divalent alkyl group that may comprise from 1 to 4 carbon atoms. As an example, we may mention methylene, propylene, isopropylene, butylene.
"saccharide unit", a radical comprising at least one radical selected from the trioses (glyceraldehyde, dihydroxyacetone), tetroses (erythrose, threose, erythrulose,), pentoses (arabinose, lyxose, ribose, deoxyribose, xylose, ribulose, xylulose), hexoses (allose, altrose, galactose, glucose, gulose, idose, mannose, talose, fructose, psicose, sorbose, tagatose), heptoses (mannoheptulose, sedoheptulose), octose (octolose, 2-keto-3-deoxy-manno-octonate), isonoses (sialose), and
"(poly)amino acid unit", a unit having at least one unit:

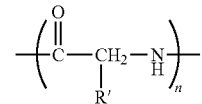

in which n is greater than or equal to 1 and R' represents a hydrogen atom, a C$_{1-6}$ alkyl group, optionally substituted with one or more hydroxyls, a C$_{1-6}$ alkoxy.

Thus, in the sense of the present invention, a "covalent bond" preferably represents a covalent bond notably such as stated above, but also covers a covalent bond represented by a linkage as defined above.

The coupling reaction necessary for establishing at least one covalent bond between at least one vitamin C molecule in question and at least one hydrocarbon radical according to the present invention may be carried out in standard conditions and its implementation is therefore clearly part of the knowledge of a person skilled in the art.

This reaction is generally carried out in solution in the presence of and with excess of at least one hydrocarbon compound considered according to the present invention with respect to the vitamin C molecule employed according to the invention, for example at a rate of two equivalents, in the standard conditions required for causing interaction of the two specific functions borne by each of the two entities.

Preferably, a starting hydrocarbon compound for synthesis of a complex according to the invention is a squalene derivative in acid form, such as for example 1,1',2-tris-norsqualenic acid, which may be prepared by the method described in example 1a.

Then, covalent coupling of the two entities of the complex according to the invention may notably be carried out as follows.

According to another aim, the present invention relates to a method of preparation (called first route hereinafter) of the complex according to the invention comprising:

condensation of at least one molecule of an acyl halide of formula (III)

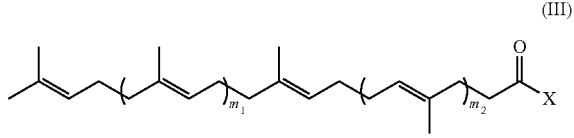

(III)

in which X is a halogen atom and preferably a chlorine atom, and $m_1$ and $m_2$ are as defined above in the compound of formula (A), and of at least one molecule of 5-(1,2-dihydroxy-ethyl)-3,4-dihydroxy-5H-furan-2-one of formula (IV)

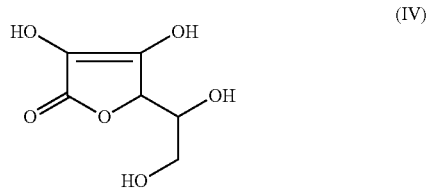 [SMILES: O=C1OC(C(O)CO)C(O)=C1O]

(IV)

to obtain said complex or conjugate according to the invention.

Preparation of the acyl halide of formula (III) starting from the corresponding carboxylic acid and a halogenating agent such as thionyl chloride $SOCl_2$, phosphorus trichloride $PCl_3$, phosphorus pentachloride $PCl_5$ and oxalyl chloride, is clearly part of the general knowledge of a person skilled in the art.

The first route of preparation of the complex according to the invention makes it possible to obtain amounts of said complex with a yield of at least 30%, or even of at least 34%, and with a degree of purity of about 90%.

According to another aim, the invention relates to a method of preparation (called second route hereinafter) of the conjugate according to the invention comprising the esterification reaction between at least one molecule of 5-(1,2-dihydroxy-ethyl)-3,4-dihydroxy-5H-furan-2-one of formula (IV)

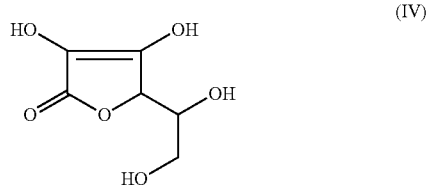 [SMILES: O=C1OC(C(O)CO)C(O)=C1O]

(IV)

and at least one molecule of an acid of formula (II)

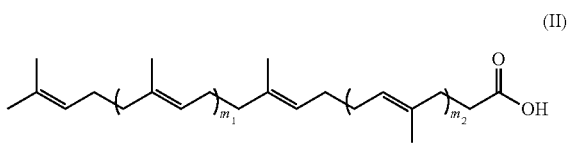

(II)

in which $m_1$ and $m_2$ are as defined above for the compound of formula (A).

Advantageously, said esterification reaction is carried out in the presence of a lipase as catalyst.

The lipases or triacylglycerol acylhydrolases are enzymes that are atypical in their mechanism of action and their substrate specificity (Fickers et al. Biotechnol. Agron. Soc. Environ. 2008, 12(2), 119-130 or Alloue et al., Biotechnol. Agron. Soc. Environ. 2008, 12(1), 57-68). They are catalysts very widely used in organic synthesis, mainly because of their stability and their activity in a solvent environment. Among the lipases according to the invention, we may notably mention the plant lipases, the mammalian lipases and the microbial lipases. According to the invention, it will be preferable to use a microbial lipase, even more preferably a lipase selected from *C. cylindracea, C. antarctica, C. miehei* and mixtures thereof, and even more preferably *a C. antarctica* lipase such as that marketed by the company Novozyme Corp with the trade name Novozyme 435®.

The second route of preparation of the complex according to the invention results in obtaining amounts of said complex with a yield less than or equal to 30% and with a degree of purity greater than or equal to 95%.

According to another aim, the present invention relates to a method of preparing the conjugate according to the invention comprising:

reaction between at least one molecule of 5-(1,2-dihydroxy-ethyl)-3,4-dihydroxy-5H-furan-2-one of formula (IV')

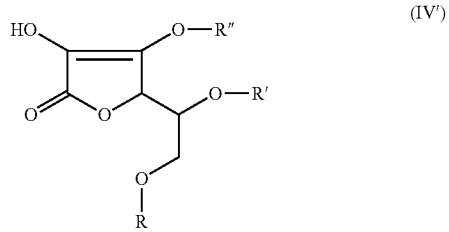

(IV')

in which R, R' and R" represent a hydrogen atom or a protective group; and at least one molecule of a compound of formula (VIII)

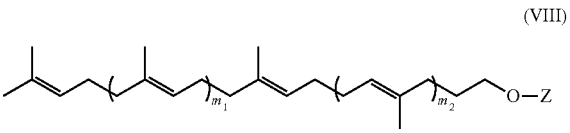

(VIII)

in which $m_1$ and $m_2$ are as defined above for the compound of formula (A); and Z is a hydrogen atom or a group $-SO_2-CH_3$.

According to a preferred embodiment, the starting hydrocarbon compound for synthesis of the conjugate according to the invention is 1,1',2-trisnorsqualenol notably as illustrated in example 1b.

Then covalent coupling of the two entities of the conjugate according to the invention may notably be carried out as follows.

A method of preparing the conjugate according to the invention comprising reaction of at least one molecule of alcohol of formula (V)

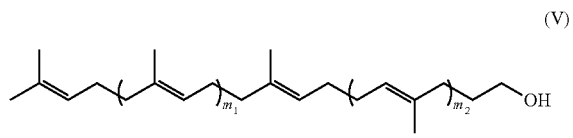

in which m1 and m2 are as defined above,
with at least one molecule derived from ascorbic acid of formula (VI)

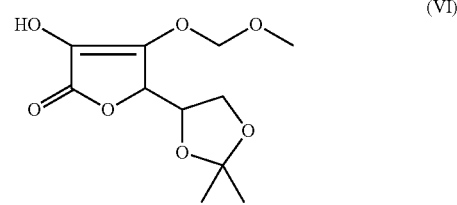 [SMILES: COCOC1=C(O)C(=O)OC1C1COC(C)(C)O1]

followed by hydrolysis to obtain said conjugate according to the invention, is also described.

According to yet another preferred embodiment, the starting hydrocarbon compound for synthesis of the conjugate according to the invention is 1,1',2-trisnorsqualenol mesylate as illustrated notably in example 1c.

Then covalent coupling of the two entities of the conjugate according to the invention may notably be carried out as follows.

A method of preparing the conjugate according to the invention comprising reaction of at least one molecule of alcohol mesylate of formula (VII)

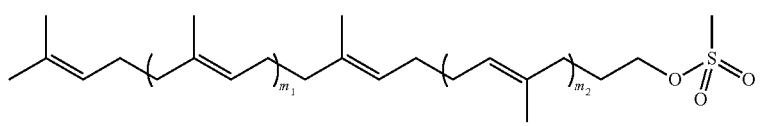

in which $m_1$ and $m_2$ are as defined above,
with at least one molecule of 5-(1,2-dihydroxy-ethyl)-3,4-dihydroxy-5H-furan-2-one of formula (IV)

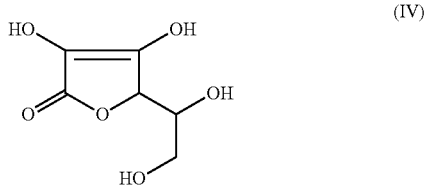

to obtain said conjugate according to the invention, is also described.

Gel According to the Invention

As mentioned above, the present invention also relates to a complex according to the invention formulated as a gel with at least one oil.

Among the oils suitable for the present invention, we may mention more particularly squalene. However, other oils may be used, provided they prove compatible with the intended applications and the complex according to the invention.

A gel formed from squalene and a complex or conjugate according to the invention notably makes it possible to obtain homogeneous formulations that may comprise up to at least 3 wt %, or even at least 10 wt %, expressed as weight of vitamin C active ingredient relative to the total weight of the composition.

Such a gel is more particularly advantageous for topical administration.

It may also be in the form of cream, unguent, ointment or of any other type of formulation known by a person skilled in the art and appropriate for the intended applications.

Nanoparticles According to the Invention

Against all expectations, the inventors found that the complex formed by covalent coupling of at least one vitamin C molecule considered according to the invention with at least one hydrocarbon compound in the sense of the invention displays capacity for self-organizing in a compact form in a polar solvent medium, and thus leads to the formation of nanoparticles.

Thus, according to another of its aspects, the present invention relates to nanoparticles of the complex according to the invention.

Generally the nanoparticles thus obtained have an average size in the range from 30 nm to 500 nm, in particular from 40 nm to 250 nm, or even from 45 nm to 95 nm measured by light scattering using the Coulter® N4MD nanosizer, Coulter Electronics, Hialeah, USA.

Thus, these particles have a size that proves compatible with any method of administration, in particular topical, injectable and oral.

As stated above, the nanoparticulate formulation is advantageous, in that it t it notably allows stabilized formulation of the complex according to the invention in an aqueous medium and increased penetration of vitamin C to the deep layers of the skin.

The nanoparticles according to the invention are, of course, able to carry a multitude of reactive functions on their surface, such as hydroxyl or amine functions for example. It is therefore conceivable to fix all kinds of molecules to these functions, notably by covalent bonds.

As illustrative, nonlimiting examples of molecules of this type that may be associated with the nanoparticles, we may notably mention molecules of the marker type, compounds able to provide a targeting function, as well as any compound able to endow them with particular pharmacokinetic characteristics. Regarding this last-mentioned aspect, we may thus envisage fixing, on the surface of these nanoparticles, lipophilic derivatives of polyethylene glycol, for example the polyethylene glycol/cholesterol conjugate, polyethylene glycol-phosphatidylethanolamine or better still polyethylene glycol/squalene. In fact, taking into account the natural affinity of the squalene residues for one another, the polyethylene glycol/squalene conjugate combines, in the present case, with the nanoparticles according to the invention, and thus leads to the formation of nanoparticles with a surface coating of polyethylene glycol. Moreover, as already mentioned, during the process of formation of the nanoparticles according to the invention, the polyethylene glycol/squalene conjugate advantageously acts as surfactant owing to its amphiphilic behavior and therefore stabilizes the colloidal suspension, thus reducing the size of the nanoparticles formed.

According to an advantageous embodiment, the nanoparticles according to the invention are formulated as an aqueous dispersion.

According to another advantageous embodiment, the nanoparticles according to the invention are in the form of lyophilizate.

Preferably, they are nanoparticles of 2-(3,4-dihydroxy-5-oxo-2,5-dihydro-furan-2-yl)-2-hydroxy-ethyl 4,8,13,17,21-pentamethyl-docosa-4,8,12,16,20-pentaenoate (also called 2-(3,4-dihydroxy-5-oxo-2,5-dihydro-furan-2-yl)-2-hydroxy-ethyl 1,1',2-trisnorsqualenate or squalenoyl-ascorbic acid or squalenoyl-vitamin C) and preferably nanoparticles of 6-squalenoyl-ascorbic acid (also called 6-squalenoyl-vitamin C).

They may also preferably be nanoparticles of (5R)-5-[(1S)-1,2-dihydroxyethyl]-4-hydroxy-3-{[(4E,8E,12E,16E)-4,8,13,17,21-pentamethyldocosa-4,8,12,16,20-pentaen-1-yl]oxy}-2,5-dihydrofuran-2-one, also called nanoparticles of 2-squalenyl-ascorbic acid or else nanoparticles of 2-squalenyl-vitamin C.

They may also preferably be nanoparticles of 5-(1,2-dihydroxyethyl)-3-hydroxy-4-{[(8E,12E,16E)-4,8,13,17,21-pentamethyldocosa-4,8,12,16,20-pentaen-1-yl]oxy}-2,5-dihydrofuran-2-one, also called nanoparticles of 3-squalenyl-ascorbic acid or else nanoparticles of 3-squalenyl-vitamin C.

Method of Preparing the Nanoparticles

More precisely, the nanoparticles are formed by bringing the complex into contact with an aqueous medium in favorable conditions for its agglomeration in the form of nanoparticles. They may notably be so-called methods of nanoprecipitation or methods of emulsion/solvent evaporation.

The nanoparticles according to the present invention may advantageously be obtained as follows.

A complex or conjugate according to the invention is dispersed in at least one organic solvent (for example an alcohol such as ethanol, or acetone) at a concentration sufficient to obtain, on adding the resultant mixture, with stirring, and generally dropwise, to an aqueous phase, the instantaneous formation of nanoparticles according to the invention in suspension in said aqueous phase. If applicable, said nanoparticles are isolated by techniques that are well known by a person skilled in the art.

Nanoprecipitation may generally be carried out at room temperature. However it is, the application temperature must not affect the activity of the vitamin C molecule in question. The method of preparing the nanoparticles according to the invention is particularly advantageous, in that it does not require the obligatory presence of surfactants.

This property is particularly desirable, as a great many surfactants are not compatible with application in vivo.

Thus, another advantage of the present invention is that no potentially toxic organic solvent or surfactant is required for production of said compositions according to the invention.

However, it is to be understood that the use of surfactants, generally advantageously devoid of any toxicity, is conceivable in the context of the invention. Surfactants of this type may moreover allow even smaller sizes to be attained during nanoparticle formation. As illustrative, nonlimiting examples of surfactants of this type that may be used in the present invention, we may notably mention polyoxyethylene-polyoxypropylene copolymers, phospholipid derivatives and lipophilic derivatives of polyethylene glycol.

As a lipophilic derivative of polyethylene glycol, we may mention for example polyethylene glycol cholesterol. As examples of the polyoxyethylene-polyoxypropylene block copolymers, we may mention in particular the polyoxyethylene-polyoxypropylene-polyoxyethylene triblock copolymers, also called Poloxamers®, Pluronics® or synperonics, which are marketed, notably, by the company BASF.

Related to these families of copolymers, the poloxamines, which consist of hydrophobic segments (based on polyoxypropylene), hydrophilic segments (based on polyoxyethylene) and a central part derived from the ethylenediamine unit, may also be used.

Composition According to the Invention

A complex and/or nanoparticles suitable for the invention may advantageously be formulated in a composition that may be in all the galenical forms normally available for the method of administration adopted.

As stated below, the choice of the form considered for the complex, namely particulate or nonparticulate, may take into account the nature of the particular galenical formulation medium considered.

Thus, in the case of a single-phase or multiphase formula such as an emulsion, the complex may advantageously be formulated as nanoparticles in the aqueous phase.

However, for a galenical form of the single-phase cream type, intended specifically for topical administration, it is advantageous to give preference to the use of a formulation of the complex according to the invention in the form of an oily gel and more particularly of the complex according to the invention mixed with squalene.

We may envisage formulating at least one complex or conjugate and/or nanoparticles according to the present invention at a rate from 0.1 to 10 wt %, expressed as weight of vitamin C active ingredient, or even more, relative to the total weight of the composition considered.

A composition of the invention comprises a physiologically acceptable medium.

"Physiologically acceptable medium" means a nontoxic medium that may be applied on the skin and is of pleasant appearance, odor and feel.

A composition of the invention may be a cosmetic, dermatological, or pharmaceutical composition.

Preferably, a composition of the invention may be administered topically.

According to one embodiment, a composition of the invention administered topically may advantageously be formulated in any galenical form suitable for the care of the skin and mucous membranes and may be in the form of unguent, creams, milks, ointments, solutions, gels, sprays, lotions, or suspensions.

A composition of the invention may also be in the form of a transdermal system permitting active or passive release of the nanoparticle(s) according to the invention by transdermal action, for example of the patch or gel patch (hydrogel) type.

These compositions are prepared by the usual methods. The formulation agents and excipients for topical compositions are known in these fields and are not described in detail here.

Advantageously, the compositions according to the invention may contain other active ingredients that may beneficially be utilized, in combination with the effect of vitamin C.

According to another aim, the present invention relates to a food supplement comprising at least one complex according to the invention or nanoparticles according to the invention.

The compositions for the oral route according to the invention may be formulated by any usual method known by a person skilled in the art for producing oral solutions, sugar-coated pills, hard capsules, gels, emulsions, tablets to be swallowed or to be crunched, capsules, notably soft or hard capsules, granules to be dissolved, syrups, solid or liquid foodstuffs and hydrogels.

A complex according to the invention and/or nanoparticles according to the invention may also be incorporated as they are in all forms of food supplements or enriched foodstuffs, for example food bars, milk drinks or non-milk drinks The examples presented below are given for purposes of illustration and are nonlimiting.

EXAMPLES

Example 1a

Preparation of 6-squalenoyl-vitamin C (VitC-SQ)

a) Synthesis of 1,1',2-tris-norsqualenic acid

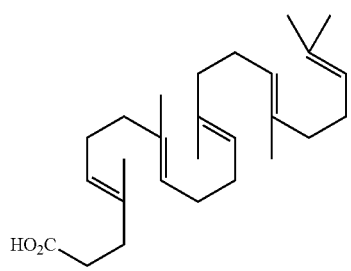 [SMILES: CC(C)=CCC/C(C)=C/CC/C(C)=C/CC/C=C(\C)CC/C=C(\C)CCC(=O)O]

2.77 g (7.2 mmol) of 1,1',2-trisnorsqualenic aldehyde (SQCHO) (Ceruti M. et al., J. Chem. Soc., Perkin Trans, 1; 2002, 1477-1486) is dissolved in 40 mL of acetone. The mixture is cooled to 0° C. in an ice bath and a solution of Jones reagent (prepared beforehand by dissolving 26.7 g of $CrO_3$ in 23 mL of concentrated $H_2SO_4$ and then extending with water up to a volume of 100 mL) is added slowly until a persistent reddish-brown coloration is obtained. A few drops of isopropanol are added to decompose the excess chromium(VI). The mixture is taken up in 30 mL of saturated aqueous NaCl solution and extracted with 4×50 mL of $Et_2O$. The organic phases are collected, washed with 30 mL of saturated aqueous NaCl solution, dried over $MgSO_4$ and then filtered. The solvents are distilled under reduced pressure, giving a yellow oil. The crude product is purified by silica chromatography (petroleum ether/diethyl ether 80/20) to give 1.34 g of trisnorsqualenic acid.

$^1$H NMR ($CDCl_3$, 300 MHz) δ: 5.19-5.07 (5H, m, vinylic CH); 2.45 (2H, t, J=7.3 Hz, $CH_2CH_2COOH$), 2.30 (2H, t, J=7.3 Hz, $CH_2CH_2COOH$), 2.09-1.98 (16H, m, allylic $CH_2$), 1.68 (3H, s, $CH_3$); 1.62 (3H, s, $CH_3$), 1.60 (12H, s, $CH_3$);

$^{13}$C NMR ($CDCl_3$, 75 MHz), δ: 180.0 (CO), 135.0 (C), 134.8 (2C), 132.8 (C), 131.1 (C), 125.3 (CH), 124.4 (2 CH), 124.2 (2 CH), 39.7 (2 $CH_2$), 39.5 ($CH_2$), 34.2 ($CH_2$) 33.0 ($CH_2$), 28.2 (2 $CH_2$), 26.8 ($CH_2$), 26.6 (2 $CH_2$), 25.6 ($CH_3$), 17.6 ($CH_3$), 16.0 (4 $CH_3$).

IR ($cm^{-1}$): 2966, 2916, 2857, 1709, 1441, 1383, 1299, 1212, 1155, 1103;

CIMS (isobutane) m/z 401 (100);

EIMS m/z (%): 400 (5), 357 (3), 331 (5), 289 (3), 208 (6), 136 (3), 81 (100)

b) Synthesis of 1,1',2-tris-norsqualenic chloride (or 4,8,13,17,21-pentamethyl-docosa-4,8,12,16,20-pentaenoyl chloride)

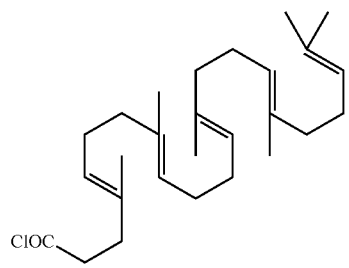

1.80g of tris-norsqualenic acid (4.5 mmol) obtained previously is dissolved in 10 mL of toluene. The solution thus obtained is degassed by passing a nitrogen stream through it. Then 1.2 mL of oxalyl chloride (1.74 g, 13.8 mmol) is added dropwise to this solution at 20° C. The mixture is stirred at room temperature for 3 h.

The solution is concentrated under reduced pressure to give the crude acid chloride of 1,1',2-tris-norsqualenic acid in the form of a yellow oil.

IR (film) δ: 2920, 1799, 1443, 1382, 955, 893;

$^1$H NMR (300 MHz, $CDCl_3$) δ (ppm): 5.23-5.10 (m, 5 H), 2.45 (t, J=7.3 Hz, 2H, $CH_2CH_2COCl$), 2.30 (t, J=7.5 Hz, 2H, $CH_2CH_2COCl$), 2.15-1.95 (m, 16 H), 1.70 (s, 3H), 1.62 (s, 15H);

$^{13}$C NMR (75 MHz, $CDCl_3$), δ (ppm): 173.2 (C, COCl), 135.1 (C, C=CH), 134.8 (C, C=CH), 134.6 (C, C=CH), 131.4 (C, C=CH), 131.1 (C, C=CH), 126.6 (CH, C=CH), 124.7 (CH, C=CH), 124.4 (CH, C=CH), 124.3 (2CH, C=CH), 45.8 ($CH_2$), 39.7 (2$CH_2$), 34.4 ($CH_2$), 34.6 ($CH_2$), 28.2 (2$CH_2$), 26.8 ($CH_2$), 26.7 ($CH_2$), 26.5 ($CH_2$), 25.7 ($CH_3$, C=C($CH_3$)$_2$), 17.6 ($CH_3$), 16.0 ($CH_3$), 15.9 (2 $CH_3$), 15.8 ($CH_3$).

c) Synthesis of 6-squalenoyl-vitamin C or 6-O-[4,8, 13,17,21-pentamethyl-docosa-4,8,12,16,20-pentaenoyl] ascorbic acid (VitC-SQ)

c-1) First Route (Condensation with the Acid Chloride Obtained in Example 1a)b))

A stream of dry hydrochloric acid HCl is bubbled until saturation in 10 mL of N-methylpiperidone (NMP) in a Durand wash bottle (caking)

The solid is dissolved by adding 10 mL of NMP. 0.70 g of ascorbic acid (4.0 mmol) is dissolved in 10 mL of the solution obtained previously and the mixture is cooled to 0° C. Then, 418 mg of the acid chloride prepared according to example 1a)b) (1.0 mmol) is added and the mixture thus obtained is stirred at room temperature for 24 h. Then 20 mL of water is added and the mixture is extracted with ethyl acetate (4×20 mL). The organic phase is washed with water (2×5 mL), dried over $MgSO_4$ and concentrated under reduced pressure. The NMP remaining in the residue is distilled under reduced pressure (0.05 mmHg, 60° C.) to give a thick residue, which is chromatographed on silica gel, eluting with ethyl acetate and then with EtOAc/MeOH mixture, 98:2 to give 6-squalenoyl-vitamin C in the form of a thick, pale yellow oil (190 mg, 34%).

c-2) Second Route (Esterification Catalyzed by a Lipase, Novozyme 435®)

Ascorbic acid (352 mg, 2 mmol) is suspended in 10 mL of anhydrous tert-amyl alcohol, followed by 300 mg of Novozyme 435® (Sigma L4777), 400 mg of tris-norsqualenic acid prepared according to example 1a)a) (1.0 mmol) and 500 mg of 4 A molecular sieve. The mixture is put in a rotary evaporator and is heated to 50° C. at 300 mbar, stirring slowly. After 48 h, the mixture is cooled, filtered on Celite and the filtrate is concentrated under reduced pressure. The residue thus obtained is chromatographed on silica gel, eluting with ethyl acetate and then with EtOAc/MeOH mixture, 98:2 to give a 6-squalenoyl-vitamin C complex in the form of a thick, pale yellow oil (167 mg, 30%).

[α]D=+10 (c=0.5, EtOH);

IR (film) ν: 2976, 2857, 1744, 1696, 1443, 1382, 1350, 1296, 1151, 1119;

$^1$H NMR (400 MHz, MeOH-d4) δ (ppm): 5.20-5.00 (m, 5H), 4.68 (d, J=1.0 Hz, 1H), 4.28-4.01 (m, 3H), 2.43 (t, J=7.3 Hz, 2H), 2.35-2.22 (m, 2H), 2.10-1.90 (m, 16H), 1.63 (s, 3H), 1.58 (s, 3H), 1.56 (s, 12H);

$^{13}$C NMR (75 MHz, CDCl$_3$), δ (ppm): 174.6 (C, CO), 173.1(C, CO), 154.8 (C, C3), 135.9 (C, C=CH), 135.8 (C, C=CH), 135.8 (C, C=CH), 134.4 (C, C=CH), 132.0 (C, C=CH), 126.5 (CH, C=CH), 125.6 (CH, C=CH), 125.5 (CH, C=CH), 125.4 (2CH, C=CH), 120.0 (C, C2), 77.1 (CH, C4), 67.9 (CH, C5), 65.7 (CH$_2$, C6), 40.8 (2CH$_2$), 40.6 (CH$_2$), 35.6 (CH$_2$), 33.9 (CH$_2$), 29.2 (2CH$_2$), 27.8 (CH$_2$), 27.7 (CH$_2$), 27.6 (CH$_2$), 26.0 (CH$_3$, C=C(CH$_3$)$_2$), 17.8 (CH$_3$), 16.3 (3CH$_3$), 16.1 (CH$_3$);

MS (+APCI) m/z (%): 559.6 (100) [M+H].

Example 1b

Preparation of 2-squalenyl ascorbic acid (2-SQ Vit C) or (5R)-5-[(1S)-1,2-dihydroxyethyl]-4-hydroxy-3-{[(4E,8E,12E,16E)-4,8,13,17,21-pentamethyldocosa-4,8,12,16,20-pentaen-1-yl]oxy}-2,5-dihydrofuran-2-one 5,6-O-Isopropylidene-L-ascorbic acid was protected in the form of methoxymethyl ether according to the procedure of Kulkami et al. (M. G. Kulkami and S. R. Thopate, Tetrahedron, 1996, 52, 1293). A Mitsunobu reaction (C. Cena et al. Bioorg. Med. Chem. 2008, 16, 5199) with 1,1',2-trisnorsqualenol followed by hydrolysis gives 2-squalenyl ascorbic acid (2-SQ Vit C) at an overall yield of 32%.

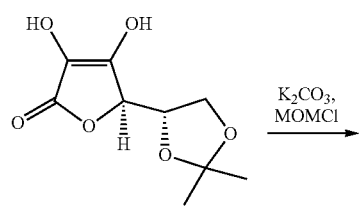

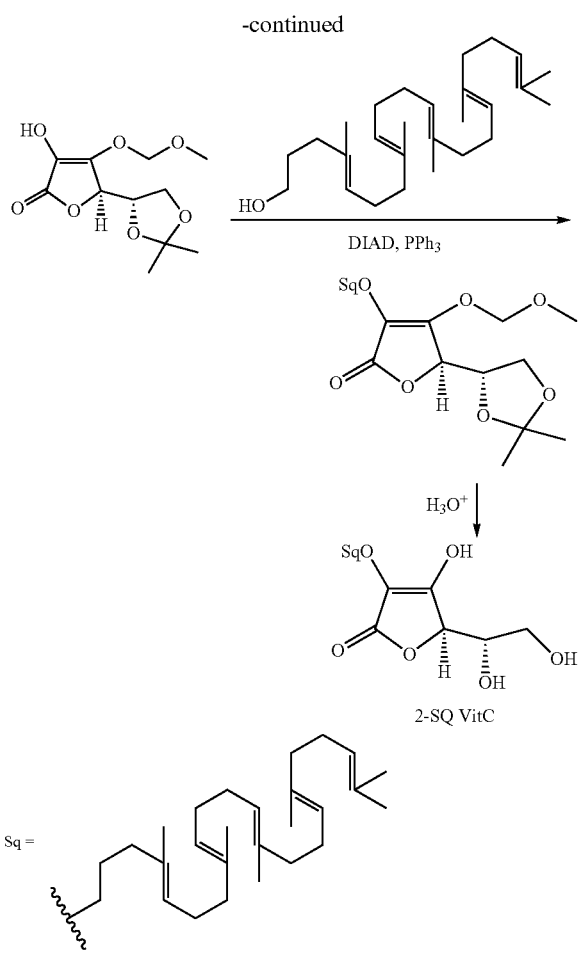

a) (5R)-5-[(4S)-2,2-dimethyl-1,3-dioxolan-4-yl]-3-hydroxy-4-(methoxymethoxy)-2,5-dihydrofuran-2-one 3.86 g of anhydrous K$_2$CO$_3$ (28 mmol) is added to a solution of 5,6-isopropylidene ascorbic acid (6.0 g, 27.7 mmol) in acetone (145 mL) and the mixture is stirred vigorously. 2.1 mL of chloro(methoxy)methane (28 mmol) in acetone (10 mL) is added dropwise over a time of two hours. Stirring is continued under reflux for a further 4 h. After cooling, the solid is filtered and washed with acetone. The filtrate was concentrated under vacuum and the residue is purified by silica gel chromatography, eluting with cyclohexane/EtOAc/acetone 6:1:1 mixture to give the compound methoxymethyl ether in the form of a white solid (4.7 g, 65%).

$^1$H NMR (CDCl$_3$, 300 MHz) δ: 7.00-6.50 (broad s, 1H, OH), 5.33 (d, J=6.02 Hz, 1H, MeOCH$_2$O), 5.31 (d, J=6.0 Hz, 1H, MeOCH$_2$O), 4.56 (d, J=3.3 Hz, 1H, H-4), 4.26 (td, J=6.7 Hz, J=3.3 Hz, 1H, H-5), 4.10 (dd, J=8.5, 6.8 Hz, 1H, H-6), 3.98 (dd, J=8.5 Hz, J=6.7 Hz, 1H, H-6), 3.54 (s, 3H, CH$_3$OCH$_2$), 1.30 (s, 3H, OC(CH$_3$)$_2$O), 1.24 (s, 3H, OC(CH$_3$)$_2$O).

b) (5R)-5-[(4S)-2,2-dimethyl-1,3-dioxolan-4-yl]-4-(methoxymethoxy)-3-{[(4E,8E,12E,16E)-4,8,13,17,21-pentamethyldocosa-4,8,12,16,20-pentaen-1-yl]oxy}-2,5-dihydrofuran-2-one 251 mg of DIAD (1.25 mmol) is added to a solution of triphenylphosphine (326 mg, 1.25 mmol) in anhydrous THF (2 mL) cooled to −15° C. After 15 minutes, a white precipitate of Mitsunobu betaine is formed. Stirring is continued for 10 minutes, then a solution of 5-(2,2-dimethyl-[1,3]dioxolan-4-yl)-3-hydroxy-4-methoxymethoxy-5H-furan-2-one (246 mg, 1.19 mmol) in THF (2 mL) is added followed by 400 mg of 1,1',2-trisnorsqualenol (1.04 mmol) in 2 mL of THF. The mixture is stirred at −15° C. for 30 min, then the reaction mixture is left to return to room temperature, continuing stirring for an additional time of 2 h. The reaction mixture is then concentrated, the residue is taken up in 20 ml of ethyl acetate and the organic phase is washed successively with a saturated solution of sodium bicarbonate (3 ml) and then with saturated NaCl solution (3 ml). The organic phases are dried over magnesium sulfate and concentrated under reduced pressure. The crude mixture is purified by silica-gel flash chromatography, eluting with cyclohexane/EtOAc mixture (1:1) to give fully protected squalenyl ascorbic acid in the form of a colorless oil (438 mg, 67%).

[α]$_D$+12.3 (c=2, CHCl$_3$);
IR (film, cm$^{-1}$) 3400, 2963, 2889, 2824, 1647, 1580, 1540, 1374, 1121, 1100, 1026;
$^1$H NMR (CDCl$_3$, 400 MHz) δ: 5.47 (d, J=5.4 Hz, 1H, OCH$_2$OCH$_3$), 5.44 (d, J=5.4 Hz, 1H, OCH$_2$OCH$_3$), 5.20-5.05 (m, 5H, =CH(CH$_3$)), 4.56 (d, J=2.8 Hz, 1H, H-4), 4.32 (td, J=6.7 Hz, J=2.8 Hz, 1H, H-5), 4.18-4.00 (m, 4H, H-6, OCH$_2$CH$_2$C(CH$_3$)), 3.52 (s, 3H, OCH$_3$), 2.12-1.95 (m, 18H, =CCH$_2$CH$_2$C(CH$_3$)), 1.82-1.74 (m, 2H, OCH$_2$CH$_2$CH$_2$C(CH$_3$)), 1.68 (s, 3H, =C(CH$_3$)$_2$), 1.61 (s, 15H, =CH(CH$_3$)), 1.39 (s, 3H, OC(CH$_3$)$_2$O), 1.36 (s, 3H, OC(CH$_3$)$_2$O);
$^{13}$C NMR (CDCl$_3$, 100 MHz) δ: 168.7 (C, C-1), 153.2 (C, C-3), 135.1 (C, =C(CH$_3$)CH$_2$), 135.0 (C, =C(CH$_3$)CH$_2$), 134.8 (C, =C(CH$_3$)CH$_2$), 134.0 (C, =C(CH$_3$)CH$_2$), 131.2 (C, =C(CH$_3$)$_2$), 124.8 (CH, =CH(CH$_3$)), 124.4 (CH, =CH(CH$_3$)), 124.3 (CH, =CH(CH$_3$)), 124.2 (2CH, =CH(CH$_3$)), 123.1 (C, C-2), 110.3 (C, OC(CH$_3$)$_2$O), 96.5 (CH$_2$, OCH$_2$O), 74.3 (CH, C-4), 73.8 (CH, C-5), 71.8 (CH$_2$, OCH$_2$CH$_2$CH$_2$C(CH$_3$)), 65.2 (CH$_2$, C-6), 57.3 (CH$_3$, OCH$_3$), 39.7 (CH$_2$, =CCH$_2$CH$_2$C(CH$_3$)), 39.6 (CH$_2$, =CCH$_2$CH$_2$C(CH$_3$)), 35.6 (CH$_2$, =CCH$_2$CH$_2$C(CH$_3$)), 28.3 (CH$_2$, =CCH$_2$CH$_2$C(CH$_3$)), 28.2 (CH$_2$, =CCH$_2$CH$_2$C(CH$_3$)), 26.7 (CH$_2$, =CCH$_2$CH$_2$C(CH$_3$)), 26.7 (CH$_2$, =CCH$_2$CH$_2$C(CH$_3$)), 26.6 (CH$_2$, =CCH$_2$CH$_2$C(CH$_3$)), 25.8 (CH$_3$, =C(CH$_3$)$_2$), 25.7 (CH$_3$, OC(CH$_3$)$_2$O), 25.6 (CH$_3$, OC(CH$_3$)$_2$O), 17.6 (CH$_3$, =CH(CH$_3$)), 16.1 (2CH$_3$, =CH(CH$_3$)), 16.0 (CH$_3$, =CH(CH$_3$)), 15.8 (CH$_3$, =CH(CH$_3$)); MS (+APCI) m/z (%): 629.7 (100) [M+H]$^+$.

c) (5R)-5-[(1S)-1,2-dihydroxyethyl]-4-hydroxy-3-{[(4E,8E,12E,16E)-4,8,13,17,21-pentamethyldocosa-4,8,12,16,20-pentaen-1-yl]oxy}-2,5-dihydrofuran-2-one (2-SQ VitC)

20 mL of 3N HCl solution is added to a solution of the above compound (400 mg, 0.63 mmol) in methanol (40 ml) and the resultant mixture is stirred at 50° C. for 4 h. The reaction mixture is then cooled to room temperature and the methanol is distilled under reduced pressure. The residue is extracted with ethyl acetate (3×50 ml). The combined organic phases are washed successively with a saturated solution of sodium bicarbonate (10 mL) and then with saturated NaCl solution (10 mL), dried over magnesium sulfate and concentrated under reduced pressure. The crude product is purified by RP-18 silica gel column chromatography, eluting with acetonitrile/water mixture (95/5) to give 2-squalenyl-ascorbic acid (260 mg, 75%).

[α]$_D$+13.4 (c=2, CHCl$_3$);
IR (film, cm$^{-1}$) 3400-3100, 1700, 1650, 1588, 1559, 1383, 1143, 1109, 1085;
$^1$H NMR (CD$_3$OD, 400 MHz) δ: 5.20-5.05 (m, 5H, =CH(CH$_3$)), 4.72 (s, 1H, H-4), 3.93 (t, J=6.0 Hz, 2H, OCH$_2$CH$_2$CH$_2$C(CH$_3$)), 3.68 (d, J=8.0 Hz, 2H, H-6), 2.12-1.94 (m, 18H, =CCH$_2$CH$_2$C(CH$_3$)), 1.84-1.73 (m, 2H$_2$OCH$_2$CH$_2$CH$_2$C(CH$_3$)), 1.67 (s, 3H, =C(CH$_3$)$_2$), 1.62 (s, 3H, =CH(CH$_3$)), 1.61 (s, 6H, =CH(CH$_3$)), 1.60 (s, 6H, =CH(CH$_3$)),
$^{13}$C NMR (CD$_3$OD, 100 MHz) δ: 174.0 (C, C-1), 165.1 (C, C-3), 136.2 (C, =C(CH$_3$)CH$_2$), 135.9 (C, =C(CH$_3$)CH$_2$), 135.8 (C, =C(CH$_3$)CH$_2$), 135.4 (C, =C(CH$_3$)CH$_2$), 132.0 (C, =C(CH$_3$)$_2$), 125.7 (CH, =CH(CH$_3$), 125.6 (CH, =CH(CH$_3$), 125.5 (CH, =CH(CH$_3$), 125.4 (2CH, =CH(CH$_3$), 121.1 (C, C-2), 77.4 (CH, C-4), 73.0 (CH$_2$, OCH$_2$CH$_2$CH$_2$C(CH$_3$)), 70.9 (CH, C-5), 63.4 (CH$_2$, C-6), 40.9 (2CH$_2$, =CCH$_2$CH$_2$C(CH$_3$)), 36.8 (CH$_2$, =CCH$_2$CH$_2$C(CH$_3$)), 29.2 (2CH$_2$, =CCH$_2$CH$_2$C(CH$_3$)), 27.8 (CH$_2$, =CCH$_2$CH$_2$C(CH$_3$)), 27.7 (CH$_2$, =CCH$_2$CH$_2$C(CH$_3$)), 27.6 (CH$_2$, =CCH$_2$CH$_2$C(CH$_3$)), 27.5 (CH$_2$, =CCH$_2$CH$_2$C(CH$_3$)), 25.9 (CH$_3$, =C(CH$_3$)$_2$), 17.8 (CH$_3$, =CH(CH$_3$)), 16.2 (3CH$_3$, =CH(CH$_3$)), 16.0 (CH$_3$, =CH(CH$_3$));
MS (−ESI) m/z (%): 543.5 (100) [M−H]$^-$.

Example 1c

Preparation of 3-squalenyl-ascorbic acid (3-SQ Vit C) or 5-(1,2-dihydroxyethyl)-3-hydroxy-4-{[(8E,12E,16E)-4,8,13,17,21-pentamethyldocosa-4,8,12,16,20-pentaen-1-yl]oxy}-2,5-dihydrofuran-2-one Direct alkylation of the mono anion of ascorbic acid with 1,1',2-trisnorsqualenol mesylate using NaHCO$_3$ as base in DMSO by the method of Beifuss (U. Beifuss et al. *Tetrahedron* 2000, 56, 357) gives 3-SQ VitC at a yield of 37% after chromatography on RP18 silica.

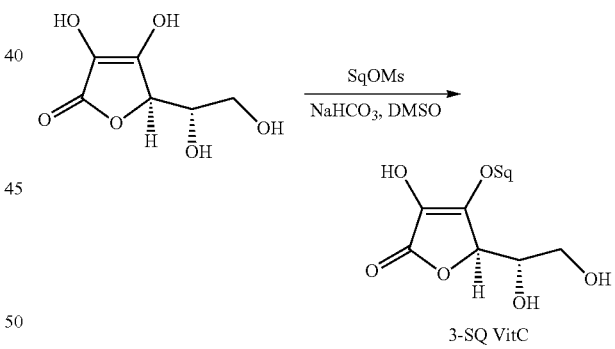

3-SQ VitC a) 4,8,12,17,21,25-(4E,8E,12E,16E)-Hexamethyl-hexacosa-4,8,12,16,20,24-hexaenyl methane-sulfonate 205 mg of Et$_3$N (2.03 mol) and 177 mg of MsCl (1.54 mmol) are added successively by syringe to a solution of 1,1',2-trisnorsqualenol (475 mg, 1.23 mmol) in dichloromethane (5 mL) cooled to 0° C. Some crystals of DMAP are added and the reaction mixture is stirred at 0° C. for 30 min and then for 1 h at 20° C. 0.1 N HCl solution (5 ml) is added and the reaction mixture is extracted with CH$_2$Cl$_2$ (3×10 ml). The combined organic phases are washed successively with a saturated solution of sodium bicarbonate (5 mL) and then with saturated NaCl solution (5 mL), dried over magnesium sulfate and concentrated under reduced pressure, giving squalenyl mesylate in the form of a pale yellow oil (582 mg, 89%). The crude mixture is used directly in the next step. $^1$H NMR (CDCl$_3$, 300 MHz) δ: 5.20-5.05 (m, 5H, =CH(CH$_3$)), 4.19 (t, J=7.0 Hz, 2H, CH$_2$OSO$_2$CH$_3$), 2.99 (s, 3H, SO$_2$CH$_3$), 2.16-1.95 (m, 18H, =CCH$_2$CH$_2$C(CH$_3$)), 1.88-1.75 (m, 2H, OCH$_2$CH$_2$CH$_2$C(CH$_3$)), 1.67 (s, 3H, =C(CH$_3$)$_2$), 1.60 (s, 15H, =CH(CH$_3$)).

b) 3-Squalenyl-ascorbic acid (3-SQ VitC) or 5-(1,2-dihydroxyethyl)-3-hydroxy-4-{[(8E,12E,16E)-4,8,13,17,21-pentamethyldocosa-4,8,12,16,20-pentaen-1-yl]oxy}-2,5-dihydrofuran-2-one 1.29 g of NaHCO$_3$ (15.4 mmol) and then 600 mg of 1,1',2-trisnor-squalenylmethanesulfonate (1.26 mmol) are added to a solution of L-ascorbic acid (776 mg, 4.4 mmol) in anhydrous DMSO (4.4 mL). The reaction mixture is stirred at 60° C. for 48 h and then concentrated under reduced pressure. The residue is treated with 2 mL of 2N HCl and extracted with ethyl acetate (3×15 ml). The combined organic phases were dried over MgSO$_4$ and the solvent is distilled under reduced pressure. The crude product is purified by RP-18 silica gel column chromatography, eluting with acetonitrile/H$_2$O mixture (95:5) to give 3-squalenyl-ascorbic acid (3-SQ Vit C) (293 mg, 37%) in the form of a pale yellow oil.

[α]$_D$+9.7 (c=3.2, CHCl$_3$);

IR (film, cm$^{-1}$) 3400, 2950-2830, 1756, 1695, 1680, 1450, 1352, 1331, 1218, 1150, 1111;

$^1$H NMR (CD$_3$OD, 300 MHz) δ: 6.00-7.00 (broad s, 1H, =C(OH)), 5.22-5.05 (m, 5H, =CH(CH$_3$)), 4.76 (d, J=1.7 Hz, 1H, H-4), 4.55-7.40 (m, 2H, OCH$_2$CH$_2$CH$_2$C(CH$_3$)), 3.87 (ddd, J=7.4, 5.9, 3.0 Hz, 2H, H-5), 3.72-3.85 (m, 2H, H-6), 2.15-1.95 (m, 18H, =CCH$_2$CH$_2$C(CH$_3$)), 1.90-1.80 (m, 2H$_2$OCH$_2$CH$_2$CH$_2$C(CH$_3$)), 1.67 (s, 3H, =C(CH$_3$)$_2$), 1.63 (s, 3H, =CH(CH$_3$)), 1.60 (s, 12H, =CH(CH$_3$));

$^{13}$C NMR (CDCl$_3$, 75 MHz) δ: 174.0 (C, C-1), 164.1 (C, C-3), 136.0 (C, =C(CH$_3$)CH$_2$), 135.9 (C, =C(CH$_3$)CH$_2$), 135.8 (C, =C(CH$_3$)CH$_2$), 135.6 (C, C-2), 135.4 (C, =C(CH$_3$)CH$_2$), 132.0 (C, =C(CH$_3$)$_2$), 125.8 (CH, =CH(CH$_3$), 125.6 (CH, =CH(CH$_3$), 125.5 (CH, =CH(CH$_3$), 125.4 (2CH, =CH(CH$_3$), 77.2 (CH, C-4), 73.0 (CH$_2$, OCH$_2$CH$_2$CH$_2$C(CH$_3$)), 70.8 (CH, C-5), 63.4 (CH$_2$, C-6), 40.9 (2CH$_2$, =CCH$_2$CH$_2$C(CH$_3$)), 36.9 (CH$_2$, =CCH$_2$CH$_2$C(CH$_3$)), 36.6 (CH$_2$, =CCH$_2$CH$_2$C(CH$_3$)), 29.2 (CH$_2$, =CCH$_2$CH$_2$C(CH$_3$)), 29.1 (CH$_2$, =CCH$_2$CH$_2$C(CH$_3$)), 27.8 (CH$_2$, =CCH$_2$CH$_2$C(CH$_3$)), 27.7 (CH$_2$, =CCH$_2$CH$_2$C(CH$_3$)), 27.6 (CH$_2$, =CCH$_2$CH$_2$C(CH$_3$)), 27.5 (CH$_2$, =CCH$_2$CH$_2$C(CH$_3$)), 25.9 (CH$_3$, =C(CH$_3$)$_2$), 17.8 (CH$_3$, =CH(CH$_3$)), 16.2 (3CH$_3$, =CH(CH$_3$)), 16.0 (CH$_3$, =CH(CH$_3$));

MS (+ESI) m/z (%): 567.6 (100) [M+Na]$^+$.

Example 2a

Preparation of the nanoparticles of 6-squalenoyl-vitamin C (VitC-SQ)

The nanoparticles are obtained by the precipitation/solvent evaporation method, by analogy with the method described in Fessi et al., Int. J. Pharm., 55, 1989, R1-R4.

A solution of 7.6 mg of vitamin C-squalenized in ethanol (0.5 mL) is added dropwise to 1 mL of an aqueous solution (MilliQ® water) at 3% of Pluronic® F68 with magnetic stirring (500 rev/min). The particles form instantaneously. The bottle containing the solution of VitC-SQ is rinsed with 0.1 mL of ethanol and the rinsing solution is added to the suspension of nanoparticles.

After stirring for 2 or 3 minutes, the suspension of nanoparticles is transferred to a calibrated 100-mL flask and is concentrated under reduced pressure in a rotary evaporator (50-100 mbar at 20° C. for 10 min and then at 37° C. for about 3-5 minutes) until the weight is 0.8-0.9 g. The solution is then made up to 1.0 g using MilliQ® water.

The nanoparticles of VitC-SQ are polydispersed in pure water.

Conversely, in the presence of 3 wt % of Pluronic® F68, the precipitation/solvent evaporation method gives nanoparticles with an average size of 51 nm with a low polydispersity (0.08). The size of the nanoparticles obtained is measured with a nanosizer (Zetasizer® from the company Malvern).

Example 2b

Preparation of the nanoparticles of 3-squalenyl-vitamin C (3-SQ VitC)

A solution of 3-SQ Vit C (5.6 mg) in 0.5 ml of ethanol is added dropwise, with stirring (500 rev/min), to 1.5 mL of milliQ water. Precipitation of the nanoparticles takes place spontaneously. Stirring is continued for 2 or 3 min. The suspension of nanoparticles is then transferred to a calibrated round-bottomed flask and the ethanol is distilled under reduced pressure (50-100 mbar) for about 10 min at room temperature and then at 30° C. for about 3-5 min. Evaporation is continued until the weight of the contents is around 1.3 to 1.4 g. The weight of the suspension is then adjusted to 1.5 g with milliQ water or 5% aqueous solution of dextrose. The average hydrodynamic diameter of the nanoparticles was determined at 20° C. by quasi-elastic light scattering at an angle of 90° with a Malvern Nanosizer (Malvern Instruments SA, Orsay, France) in a quartz cuvette (path length 10 mm). The samples were prepared by 10-fold dilution of the mother solution in water. The average hydrodynamic diameter is given as weighted number over all the populations (Z mean). An average diameter of 69 nm with a polydispersity index of 0.22 was observed. The nanoparticles are stable for a period of three days.

Example 3

Preparation of the gel of 6-squalenoyl-vitamin C (VitC-SQ) in squalene

In a 5-mL tablet bottle, 110 mg of squalene (0.27 mmol) is added to 15 mg of VitC-SQ obtained according to example 1a (0.027 mmol). The mixture is stirred vigorously for 2 min at 40° C., and is then sonicated in an ultrasonic tank for 1 min. After cooling, a homogeneous gel is obtained at 3 wt % expressed as weight of vitamin C, or 10 mo of VitC-SQ.

Example 4

Evaluation of the "Anti-Aging" Activity of the VitC-SQ Complex

Explants of human skin with a diameter of about 10 nm, obtained from surgical waste from cosmetic surgery and more particularly from abdominoplasty of women about thirty years of age, are used. The human skin is kept alive in a usual nutrient medium at 37° C. in humid atmosphere, enriched with 5% CO$_2$, for ten days.

The explants of human skin are treated using a gel according to the invention comprising the VitC-SQ complex or conjugate according to the invention obtained in example 1a formulated in squalene as described in example 3 to obtain compositions comprising 1 wt % and 3 wt % respectively, expressed as weight of vitamin C active ingredient relative to the total weight of the composition. To obtain values of 1% and 3% respectively, expressed as weight of vitamin C, the concentration of the VitC-SQ complex is adjusted accordingly.

In parallel, three control tests are carried out.

The first control test consists of explants of human skin that have not been treated (control No. 0).

The other two control tests employ, respectively, as vitamin C derivative, "free" vitamin C (control No. 1) and a vitamin C-palmitate derivative, also called VitC-palm hereinafter (control No. 2), which may notably be supplied by the companies Sigma-Aldrich or Alpha Aesar. These two active ingredients are used at a concentration of 1 wt % and 3 wt %, expressed as weight of vitamin C active ingredient relative to the total weight of the composition.

A gel comprising the VitC-Palm derivative formulated in squalene is prepared by the method given in example 3 in which VitC-SQ is replaced with VitC-Palm.

To prepare a gel containing "free" vitamin C, 20 g of sterile distilled water is put in a 50-mL beaker and is heated to 50° C. Then 50 mg of preservative is added, followed by 200 mg of crystalline vitamin C, with mechanical stirring. Next, 400 mg of carboxymethyl cellulose (notably supplied by the company Sigma-Aldrich) is added in small portions, avoiding formation of lumps. Heating is stopped and it is made up to the initial weight. Then it is left to cool, stirring gently until the gel forms. Finally, the gel obtained is transferred to an airtight bottle.

Each of the compositions tested is applied topically, at a rate of 2 mg per explant, on the explants of human skin using a spatula on day zero (DO), then at 1 day (D1), at 3 days (D3), at 6 days (D6) and finally at 8 days (D8).

On day zero, the explants of control No. 0 are taken and each explant is cut into two parts. One half is fixed in ordinary Bouin and the other half is frozen at −80° C.

On the tenth day, the explants treated with each of the compositions are taken and are submitted to the same conditions as the explants of control No. 0.

After 48 hours of fixation in ordinary Bouin, the samples are dehydrated and impregnated with paraffin using a Leica 1020 automatic dehydrator. Then they are made into a block according to procedure MO-H-153 using a Leica EG 1160 coating station.

5-μm sections are prepared using a Minot type microtome, Leica RM 2125, and are glued on superfrost silanized glass histology slides.

Microscopic observations are performed in light microscopy, using a Leica microscope of the Orthoplan type, with x 25 and x 40 objectives. The images are recorded with a Sony DXC 390P tri CCD camera and are stored using Leica IM1000 data archiving software.

The effect of each of the active ingredients is characterized as follows.

a) Evaluation of Acanthosis

Acanthosis of the skin, and more generally observation of the general morphology is carried out on sections in paraffin after staining with Masson's trichrome, Goldner's variant, according to procedure MO-H-157.

At time T0, i.e. before topical application of the compositions, it is observed that the stratum corneum is thick, very slightly laminated, slightly keratinized on the surface and at its base.

Moreover, the epidermis has 4 to 5 layers with good morphology and the relief of the dermal-epidermal junction is sharp.

Moreover, the papillary dermis shows thick collagen fibers forming a more or less dense network that is well cellularized.

These observations are of course similar for the untreated explants of control No. 0.

On the tenth day (D10), for the untreated explants (control No. 0), the general morphology is similar to that observed at T0.

b) Evaluation of the Expression of GAGs.

Neutral GAGs, reservoirs of the growth factors near the dermal-epidermal junction, and acid GAGs, essentially hyaluronic acid, are examined on paraffin sections after staining with alcian blue/PAS (Mowry staining)

Before topical application of the compositions (T0), which also applies to the untreated explants (control No. 0), it is observed that the neutral GAGs are very moderate, forming a very irregular pink/purplish band of small thickness along the dermal-epidermal junction. Moreover, they are slight in the underlying papillary dermis.

Moreover, the acid GAGs are not moderate in the epidermal intercellular spaces as well as in the papillary dermis.

On D10, for the untreated explants (control No. 0), expression of the neutral GAGs is slightly increased relative to that observed at T0 and the acid GAGs are very moderately overexpressed in the epidermal intercellular spaces.

The observations made on D10 relative to the control No. 0, concerning the treated explants, are summarized in the following table:

| Explants treated | Observations |
| --- | --- |
| VitC-SQ according to the invention at 1% | Slight epidermal stimulation<br>Moderate dermal stimulation<br>Slight overexpression of neutral GAGs<br>No overexpression of the epidermal acid GAGs |
| VitC-SQ according to the invention at 3% | Definite epidermal stimulation<br>Fairly definite dermal stimulation<br>Definite overexpression of neutral GAGs<br>No overexpression of epidermal acid GAGs |
| Free vitamin C at 1% (control No. 1) | No epidermal stimulation<br>No dermal stimulation<br>No overexpression of neutral GAGs<br>No overexpression of epidermal acid GAGs |
| Free vitamin C at 3% (control No. 1) | No epidermal stimulation<br>Moderate dermal stimulation<br>No overexpression of neutral GAGs<br>No overexpression of epidermal acid GAGs |
| VitC-palm at 1% (control No. 2) | No epidermal stimulation<br>No dermal stimulation<br>Slight overexpression of neutral GAGs<br>No overexpression of epidermal acid GAGs |
| VitC-palm at 3% (control No. 2) | No epidermal stimulation<br>Moderate dermal stimulation<br>Very moderate overexpression of neutral GAGs<br>No overexpression of epidermal acid GAGs | c) Evaluation of Expression of Type III Collagen and type I Collagen.

For this assessment, only certain of the explants of human skin described above are used. More particularly, they are untreated explants (control No. 0) and explants treated with VitC-SQ according to the invention at 3 wt %, with free vitamin C at 3 wt % (control No. 1) and with VitC-palm at 3 wt % (control No. 2), expressed as weight of vitamin C active ingredient relative to the total weight of the composition.

The microscopic observations are carried out in light microscopy, using a Leica microscope, type DMLB, with x 40 objective. The images were recorded with an Olympus DP72 camera, using Olympus Cell^D acquisition and archiving software.

Type I collagen is labeled on frozen sections with a rabbit anti-human collagen I antibody (Monosan ref PS047, polyclonal), at 1/800th for 1 hour at room temperature with a biotin/streptavidin amplifier system, detected by fluorescence (FITC caltag SA 1001). The nuclei were counterstained with propidium iodide.

Regarding the labeling of type III collagen, the latter is labeled on sections in paraffin (fixation with formol) with a goat anti-human collagen III polyclonal antibody (SBA ref: 1330-01), at 1/50th overnight at room temperature using a Vectastain RTU Universal VECTOR avidin/biotin amplifier system, detected in diaminobenzidine (DAB) with the nuclei counterstained with Masson's hemalum.

Regarding type I collagen, for the untreated explants (control No. 0), on the tenth day, labeling is fairly definite and fairly dense in the whole papillary dermis.

For the type III collagen, for the control No. 0 explants, on the tenth day, labeling is slight to moderate and fairly regular in the whole papillary dermis.

The observations made on D10, relative to the control No. 0, concerning the treated explants, are summarized in the following table:

| Explants treated | Observations |
| --- | --- |
| VitC-SQ according to the invention at 3% | Slight underexpression of type I collagen<br>Slight overexpression of type III collagen |
| Free vitamin C at 3% (control No. 1) | No overexpression of type I collagen<br>No overexpression of type III collagen |
| VitC-palm at 3% (control No. 2) | No overexpression of type I collagen<br>Very slight overexpression of type III collagen |

Firstly, it is noted that there is no effect of "free" vitamin C at a dose less than or equal to 3 wt %, expressed as weight of vitamin C active ingredient relative to the total weight of the composition.

Only the complex according to the invention displays a significant effect at a dose of 3 wt % relative to the total weight of the composition.

Consequently, these results reveal that the presence of the squalenoyl radical, against all expectations, increases the efficacy of vitamin C down to the deep layers of the skin, since it proves effective at a concentration below the concentration usually required.

For all of the tests carried out starting from 3% of active substance, thickening of the skin is observed, with a fairly significant densification of the collagen in the papillary dermis. The neutral GAGs are also overexpressed significantly along the dermal-epidermal junction and type III collagen is overexpressed at the expense of type I collagen.

However, these phenomena are significantly exacerbated with the complex according to the invention.

Thus, it is found that at equivalent dose of vitamin C, the VitC-SQ derivatives allow dermal and epidermal stimulation greater than VitC-Palm.

Moreover, it was found that there is definite overexpression of neutral GAGs and overexpression of type III collagen to the detriment of type I collagen relative to the compositions comprising VitC-Palm or "free" vitamin C.

Owing to the presence of a large amount of GAGs, polysaccharides having a high capacity for water retention, and of type III collagen in the skin, the morphology of the skin is improved. The skin appears thick, with a flexible, elastic texture, and hydrated.

Thus, the complex according to the invention displays anti-aging activity greater than the VitC-Palm commercial derivative.

Example 5

Results for Cytotoxicity of the VitC-SQ Complex

Test of Cellular Viability (MTT Assay)

10 000 cells of CCD34SK human fibroblasts per well were seeded in a 96-well plate.

The test products are added to the wells in different concentrations. After 4 h of incubation, the culture medium is replaced with new biological medium and the cells are incubated for 48h at 37° C. and 5% $CO_2$.

Then, the culture medium is removed by inverting and 100 μL, of PBS/well with MTT at a concentration of 0.5 mg/ml is added. The plate is put back in the incubator for 2 h at 37° C. and 5% $CO_2$. In order to dissolve the dark blue crystals of formazan that have formed, 100 μL of a solution of SDS (sodium dodecyl sulfate) is added to each well and then the plate is incubated again for 12 h at 37° C. and 5% $CO_2$.

At the end of the 12 h, spectrophotometric measurements are carried out on an ELISA plate reader at a wavelength of 570 nm. The percentage viability of the cells in the presence of the test molecules is then calculated from the following formula: (mean OD of the treated cells—OD of control with medium only/mean OD of the control cells (100% viability)—OD of control with medium only)×100±standard deviation; or presented in the form of curves plotting the evolution of absorbance as a function of time.

The IC50 values ("inhibitory concentration 50%" or the concentration that inhibits growth of 50% of the cells) then correspond to a product concentration tested generating a loss of 50% in cellular viability (see Table below).

TABLE

IC50 (μM). Biological activity in vitro of VitC-SQ, VitC and VitC-palm on the lines of CCD34SK human fibroblasts.

| Product tested | IC50, μM |
| --- | --- |
| VitC-SQ | 600 |
| VitC-palm | 250 |
| VitC | ND |

Results:

Based on the results obtained, toxicity of VitC has not been determined. VitC-SQ is half as toxic as VitC-palm.

The invention claimed is:

1. A conjugate formed from at least one molecule of 5-(1,2-dihydroxy-ethyl)-3,4-dihydroxy-5H-furan-2-one of formula (IV)

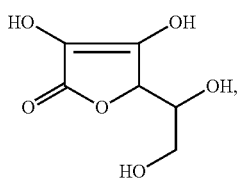
(IV)

enantiomers, diastereoisomers, or racemic mixtures thereof, bound covalently to at least one hydrocarbon radical of formula (A) as follows:

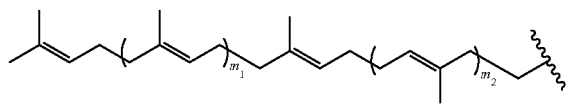
(A)

in which:
$m_1$=1, 2, 3, 4, 5 or 6;
$m_2$=0, 1, 2, 3, 4, 5 or 6; and

represents the site of binding to the molecule of 5-(1,2-dihydroxy-ethyl)-3,4-dihydroxy-5H-furan-2-one of the formula (IV) or the enantiomer, diastereoisomer, or racemic mixture thereof, the at least one hydrocarbon radical of the formula (A) being fixed by a covalent bond to at least one hydroxyl group of the 5-(1,2-dihydroxy-ethyl)-3,4-dihydroxy-5H-furan-2-one of the formula (IV).

2. The conjugate as claimed in claim 1, wherein the hydrocarbon radical comprises from 12 to 40 carbon atoms.

3. The conjugate as claimed in claim 1, wherein the hydrocarbon radical is the radical of formula (A) in which $m_1$ represents 1 and $m_2$ represents 2, or $m_1$ represents 0 and $m_2$ represents 0, or $m_1$ represents 1 and $m_2$ represents 0.

4. The conjugate as claimed in claim 1, wherein the conjugate is represented by the following formula (I):

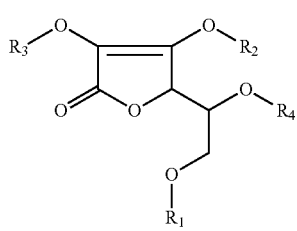
(I)

in which:
$R_1$, $R_2$, $R_3$ and $R_4$, which may be identical or different, represent independently of one another a hydrogen atom or a hydrocarbon radical of formula (A) as claimed in claim 1, and
at least one of the groups $R_1$, $R_2$, $R_3$ and $R_4$ are not a hydrogen atom.

5. The conjugate as claimed in claim 1, wherein the conjugate is represented by the following formula (IA):

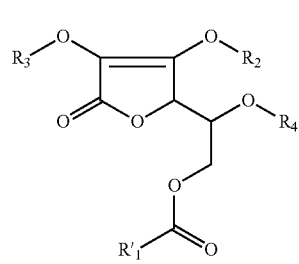
(IA)

in which:
$R_2$, $R_3$ and $R_4$, which may be identical or different, represent independently of one another a hydrogen atom or the hydrocarbon radical of the formula (A) as claimed in claim 1, and
$R'_1$ represents the hydrocarbon radical of the formula (A) as claimed in claim 1.

6. The conjugate as claimed in claim 5, wherein all three of $R_2$, $R_3$ and $R_4$ represent a hydrogen atom.

7. A method of preparing a conjugate as claimed in claim 1, the method comprising:
condensation of:
at least one molecule of an acyl halide of the following formula (III)

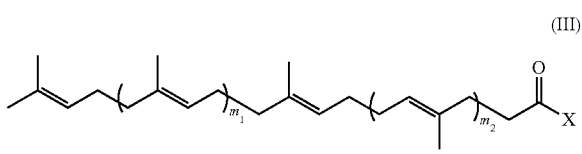
(III)

in which X is a halogen atom, and $m_1$ and $m_2$ are as defined for the hydrocarbon radical of formula (A) as claimed in claim 1, and of
the at least one molecule of 5-(1,2-dihydroxy-ethyl)-3,4-dihydroxy-5H-furan-2-one of the formula (IV) as claimed in claim 1.

8. A method of preparing the conjugate as claimed in claim 1, the method comprising:
an esterification reaction between:
the at least one molecule of 5-(1,2-dihydroxy-ethyl)-3,4-dihydroxy-5H-furan-2-one of the formula (IV) as claimed in claim 1, and
at least one molecule of an acid of the following formula (II):

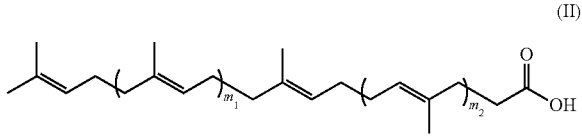
(II)

in which $m_1$ and $m_2$ are as defined for the hydrocarbon radical of the formula (A) as claimed in claim 1.

9. A method of preparing the conjugate as claimed in claim 1, the method comprising:
reaction between:
at least one molecule of 5-(1,2-dihydroxy-ethyl)-3,4-dihydroxy-5H-furan-2-one of the following formula (IV'):

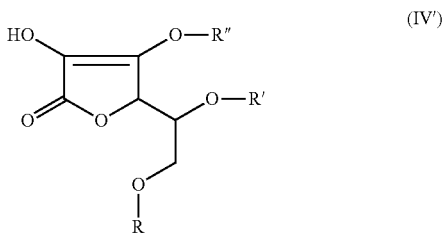

in which R, R' and R" represent a hydrogen atom or a protective group; and
at least one molecule of a compound of the following formula (VIII):

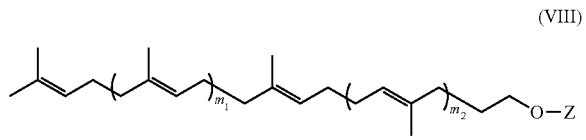

in which $m_1$ and $m_2$ are as defined for the hydrogen radical of the formula (A) as claimed in claim 1; and Z is a hydrogen atom or a group —$SO_2$—$CH_3$.

10. The conjugate as claimed in claim 1 formulated as a gel with at least one oil.

11. Nanoparticles of the conjugate as defined in claim 1.

12. The nanoparticles as claimed in claim 11, wherein the conjugate is 6-squalenoyl-vitamin C.

13. The nanoparticles as claimed in claim 11, wherein the conjugate is 2-squalenyl-vitamin C.

14. The nanoparticles as claimed in claim 11, wherein the conjugate is 3-squalenyl-vitamin C.

15. The nanoparticles as claimed in claim 11, wherein the nanoparticles have an average size in the range from 30 nm to 500 nm.

16. A method of preparing the nanoparticles as claimed in claim 11, the method comprising at least:
dispersion of the conjugate in at least one organic solvent at a concentration sufficient to obtain, on adding the corresponding mixture, with stirring, to an aqueous phase, instantaneous formation of nanoparticles in suspension in said aqueous phase, and
isolation of said nanoparticles.

17. A cosmetic, dermatological or food composition comprising as active substance at least one conjugate as claimed in claim 1 and/or nanoparticles of the conjugate as defined in claim 1 together with at least one physiologically acceptable vehicle.

18. A cosmetic process for treating the signs of aging of the skin of the body and/or of the face using the conjugate as claimed in claim 1 and/or nanoparticles of the conjugate as defined in claim 1.

19. A cosmetic process for stimulating the synthesis of collagen and/or for stimulating the synthesis of glycosaminoglycans using the conjugate as claimed in claim 1 and/or nanoparticles of the conjugate as defined in claim 1.

20. A medicament comprising as active substance at least one conjugate as claimed in claim 1 and/or nanoparticles of the conjugate as defined in claim 1.

21. A process for treating burns and/or wounds using the conjugate as claimed in claim 1 and/or nanoparticles of the conjugate as defined in claim 1.

22. A method of cosmetic treatment of the skin of the body and/or of the face and/or of the scalp, the method comprising:
administering the composition as defined in claim 17.

* * * * *